United States Patent [19]

Edwards

[11] 4,402,971

[45] Sep. 6, 1983

[54] PARA-ANISOLE-CONTAINING BIOCIDE AND METHOD FOR ISOLATING IT AND USING IT

[75] Inventor: Kent R. Edwards, Mendota Heights, Minn.

[73] Assignee: H. B. Fuller Company, St. Paul, Minn.

[21] Appl. No.: 218,290

[22] Filed: Dec. 19, 1980

[51] Int. Cl.$^3$ .................. A01N 43/08; C07D 317/48
[52] U.S. Cl. .................................. 424/279; 549/313; 549/323
[58] Field of Search ............... 260/340.5 R, 340.50 D, 260/343.6; 424/279, 282, 279; 549/313, 323

[56] References Cited

U.S. PATENT DOCUMENTS

| | | | |
|---|---|---|---|
| 2,776,239 | 1/1957 | Rowlands | 260/340.5 R |
| 2,870,164 | 1/1959 | Klohs et al. | 260/340.5 R |
| 3,057,876 | 10/1962 | Wagner | 260/340.5 R |
| 3,210,376 | 10/1965 | Smith | 260/343.6 |
| 3,287,459 | 11/1966 | Zimmer et al. | 260/343.6 |
| 3,704,247 | 11/1972 | Munakata | 260/340.5 |
| 3,896,234 | 7/1975 | Sutton | 424/279 |
| 4,196,127 | 4/1980 | Johnson et al. | 568/648 X |

FOREIGN PATENT DOCUMENTS 112884  5/1975 German Democratic Rep. .

OTHER PUBLICATIONS

Anjaneyulu et al., Indian J. Chem., vol. 11 (Mar. 1973), pp. 203–206.
Schrecker et al., Journ. Amer. Chem. Soc. 74, pp. 5672–5675.
Chem. Abstracts 68:95728j.
Mason, "Blue-Green Algal (Cyanophyta) Toxins", Minn. Acad. Science, vol. 45(2), pp. 12–13 (1979).
Iino et al., Agr. Biol. Chem., 36 (13), pp. 2505–2509 (1972).
Elleman et al., Aust. J. Biol. Sci., 31 (1978), pp. 209–218).
Alam, J., Environ. Sci. Health, A13(7), pp. 493–499 (1978).
Allen, M., J. Phycol. 4, 1–4 (1968).
Chan et al., Marine Biology 59, pp. 7–13 (1980).
Mason et al., J. Phycol., Jun. 1980, vol. 16, p. 27 (Abstract No. 97).
Mason, Minn. Acad. Science, Abstracts of Papers, Apr. 25–26, p. 1 (1980).
Mason et al., J. Phycol., No. 15, Jun. 1979, p. 20 (Abstract No. 44).
Mason, O. P., Minn. Acad. Science, Abstracts of Papers, May 4–5, 1979.
Chemistry of Lichen Substances, Yasuhiko Asahina (1954).
Chemical & Botanical Guide to Lichen Products, Culherson (1969).
"Facets of Freshwater", Freshwater Biol. Institute, vol. 5, No. 3, pp. 1–2 (1980).
Chem. Abstracts 84:116942x.

Primary Examiner—Ethel G. Love
Attorney, Agent, or Firm—Merchant, Gould, Smith, Edell, Welter & Schmidt

[57] ABSTRACT

At least one algae-produced, substantially pure chemical compound with biocidal activity has been isolated from a blue-green algal (Cyanobacteria) toxin, preferably Scytonema toxin. This biocide appears to be one of the first of its class, since very little is now known regarding algal toxins and any biocides (including any antibiotics) they may contain. A biocide of this invention has activity against harmful blue-green algae such as Anabaena and can be used as, among other things, an algicide with minimal undesirable effects upon the environment of use (e.g. lakes, streams, water supplies, swimming pools, etc.). An ether-soluble, nonsteroidal, anisole-containing biocide of this invention appears to have a molecular weight of 430 or 431, a melting point or range within the range of about 48° to about 55° C., and the empirical formula $C_{23}H_{23}O_6Cl$. Other groups in the molecule besides the anisole appear to include a saturated gamma-lactone, an aliphatic OH, a methylene bridge, a chlorobenzene ring, and an isopropyl substituent (probably attached to the gamma-lactone) in an asymmetric environment. The compound can be stored in or crystallized from diethyl ether and blended with the usual pharmaceutical extenders.

5 Claims, No Drawings

PARA-ANISOLE-CONTAINING BIOCIDE AND METHOD FOR ISOLATING IT AND USING IT

TECHNICAL FIELD

This invention relates to a new class of substantially pure, nonsteroidal biocidal compounds which occur in nature in impure or combined form as part of a toxin secreted by algae. An aspect of this invention relates to a new biocidal compound the structure of which is not precisely known but which is believed to have several distinguishing moieties or functional groupings, including a para-linked anisole group, a saturated gamma-lactone, an aliphatic hydroxyl group, and a chlorinated aromatic nucleus. Still another aspect of this invention relates to biocidal (including antibiotic) compositions containing a biocide of this invention.

DESCRIPTION OF THE PRIOR ART

The search for new biocidal compounds (including antibiotics which are, in a sense, biocides active against microorganisms and administered in vivo) has been a constantly active and ever-expanding one since the early part of this century. Many branches of the biological sciences have contributed findings to this search. One such contribution came recently from a botanist studying the ability of certain species of blue-green algae growing in lakes to compete effectively with their better-established algal neighbors. The botanist, Dr. Charles Mason grew a "streak" of one species of blue-green algae in a covered glass dish and then added a second species, Scytonema hoffmanii, as a "cross streak". After a week, a clear zone appeared at the intersection of the streaks, indicating that the second algae species had killed off the first. In short, some of these blue-green algae species survive by killing off neighboring colonies of other species which might inhibit them. Mason's discovery suggested that a toxin active against blue-green algae may be produced in nature by certain species of the algae themselves. Such discocveries of "naturally" synthesized toxins can be a very welcome contribution. The toxin is produced in nature, so it is probably biodegradable and theoretically should not build up in the environment even if applied repeatedly by man, e.g. by continual treatment of lakes and streams.

Present indications are that the Syctonema toxin discovered by Mason is nonmutagenic and probably not likely to harm desirable plants and animals. The activity of this toxin against several blue-green algae species has been confirmed by various tests and reported in the scientific literature. Some studies also suggest the possibility of other useful antibiotic activity.

The blue-green algicide activity would be in itself a more than adequate justification for the use of this toxin on a commercial scale. For many years, water supplies and lakes and streams have been plagued with undesirable effects caused by a variety of blue-green algae including species of the genus Anabaena. Mason's Scytonema toxin has been shown to be active against, among other undesirable algal organisms, several of these Anabaena species. Thus, this Scytonema toxin has the potential of providing an antibiotic which could aid in the control of blue-green algae that build up in water supplies and even clog drinking water pipes in tropical countries.

The discoveries of Dr. Mason and his coworkers have raised several questions. Is there one or more distinct chemical compounds which can be isolated from the Scytonema toxin? If not, what is the chemical or biological mechanism which causes this toxin to be so active? If one or more chemical compounds can be isolated from the toxin, will these compounds be active in the absence of the biological environment which produced them?

The pharmaceutical industry has had a considerable amount of experience with bacteria and fungi which produce antibiotic substances. Such "natural" antibiotics have probably developed in nature in order to enable these microorganisms to gain an advantage in a natural habitat over competing organisms. Dr. Mason's discoveries with respect to the Scytonema toxin appear to bear some analogy to this experience with bacteria and fungi; however, the amount of information presently available on algal toxins or antibiotics is so meager that more evidence is needed to draw any analogy to conventional antibiotics.

SUMMARY OF THE INVENTION

It has now been found that at least one algal biocide or antibiotic can be isolated from algal cellular material in a manner which preserves or enhances its biocidal activity, thus providing a distinct chemical compound which can, if desired, be combined with pharmaceutical extenders, excipients, etc. to provide a useful chemical agent for the control of, among other organisms, blue-green algae (Cyano-bacteria). Thus, at least one chemical compound can be isolated in substantially pure form, and this compound has the desired biocidal activity. The isolation of this compound does not preclude the possibility that other useful chemical compounds may exist in the Scytonema, also in an impure or combined form. But the available evidence does confirm that the single chemical compound isolated and purified in accordance with this invention has excellent biocidal activity in and of itself, i.e. in the absence of any such additional active chemical compounds.

The biocidally active compound of this invention in its substantially pure form has the empirical formula $C_{23}H_{23}O_6Cl$. The molecular weight of the compound as determined by mass spectroscopy is approximately 430, indicating that the structure of the compound is not a multiple of the aforementioned $C_{23}$ formula. Very few known compounds have 23 carbons, 23 hydrogens, 6 oxygens, and 1 chlorine, and of these very few compounds, at least one is a steroid. The biocidal compound of this invention, however, is nonsteroidal.

This compound has a melting point within the range of about 48° to about 55° C. and dissolves readily in diethyl ether. By various analytical techniques, including nuclear magnetic resonance (NMR), infrared spectroscopy, and mass spectroscopy, the presence of at least the following functional groupings has been detected:

(a) a para-linked anisole group,
(b) a saturated gamma-lactone,
(c) an aliphatic hydroxyl group,
(d) a methylene bridge,
(e) a chlorine atom substituted on an aromatic nucleus, and
(f) an isopropyl substituent in an asymmetric environment.

The presently preferred method for making the compound involves extracting biocidal material from an active constituent of Scytonema Sp. or its growth medium with a liquid organic solvent such as diethylether, and subjecting the thus-obtained extract to at least one chromatographic separation procedure, preferably a plurality of such procedures.

Although the compound is substantially insoluble in water, the compound can be readily stored, shipped, and dispensed in ether solution. The compound is stable in such solutions and is also stable at ordinary temperatures and moderately elevated temperatures. Crystals of the compound can be extended with conventional inert powdered materials such as talc and other solid, particulate pharmaceutical extenders.

DETAILED DESCRIPTION

Available analytical evidence indicates that the para-anisole group is linked to the saturated gamma-lactone by a —CH= bridge. This gamma-lactone has an unusual structure which may include one or zerhaps two chyrocenters (asymmetric or optically active centers). One of the carbons of the gamma-lactone is believed to have a hydroxyl substituent, thereby explaining the detection of an aliphatic OH. Still another substituent believed to be present on the gamma-lactone is an isopropyl substituent in an asymmetric environment. It is believed that this isopropyl substituent is substituted on the carbon which bears the hydroxyl substituent. The gamma-lactone appears to be linked to a fused-ring structure by a methylene bridge. This fused-ring structure is believed to comprise a disubstituted 1,3-benzodioxole (i.e. a disubstituted 1,2-methylenedioxybenzene), one of the substituents being the methylene bridge, the other being the chlorine.

The positioning of these substituents appears to be as follows. The para position of the anisole groups is linked via the —CH= bridge to the carbon gamma to the carbonyl of the lactone. The beta-carbon of the lactone is believed to be substituted with the hydroxyl group and the isopropyl group. The alpha-carbon is believed to be linked to the fused-ring system via the methylene bridge. The chlorine of the chlorobenzene ring is believed to be attached ortho to the carbon of the benzene ring which is attached to the methylene bridge, but other positionings are possible. A dioxole ring appears to be fused to adjacent positions on the chlorobenzene ring, resulting in the benzodioxole structure.

The para-anisole and the dioxole functional groupings may explain the ready solubility of this compound in diethyl ether.

PREPARATION OF THE PURE COMPOUND

At the present time, the preferred species for biosynthetic formation of the compound is *Scytonema hoffmanii*, an organism which has been on deposit at a University of Texas culture collection for quite some time. The University of Texas Deposit Number is 1581.

Researchers have shown that this preferred species can be grown in large quantities. See, for example, Facets of Freshwater 5:1 (1980). The resulting cellular material can be broken up into cell fragments by any suitable conventional technique (mechanical, ultrasonic, etc.). The cell debris is then centrifuged out, and the remaining liquid is lyophilized. This lyophilized material is treated with diethyl ether to extract a concentrate which has been found to contain the biocidal compound of this invention. This concentrate (hereinafter referred to as the "ether extract") is itself active, as is the lyophilized material.

The ether extract is then chromatographed using thin-layer chromatography (TLC), the preferred TLC medium being silica gel coated on a glass plate, a typical silica gel thickness being on the order of 2,000 micrometers. Distinct active bands are found by TLC when the ether extract on the plate is developed with first acetone and then chloroform; however many other single solvents or mixtures or sequences of solvents can be used, as will be apparent from the solubilities discussed subsequently. The active bands are then subject to high pressure liquid chromatography (HPLC) which results in the isolation of a single active component. This single component is a unique chemical compound—the compound of this invention. This compound has high biocidal activity and appears to be present in the preferred Scytonema in relatively large quantities compared to some other compounds which may be easier to isolate and which are also active. The degree of difficulty of isolating the compound of this invention is believed to pose no commercial scale-up difficulties of any significance, however, and its higher level of production by the organism is considered to be a definite advantage in a commercial context.

As noted previously, the new class of substantially pure, nonsteroidal biocidal compounds obtained according to this invention are readily soluble in diethyl ether. Their solubility in $CCl_4$, $CHCl_3$, $CH_3COCH_3$, $CH_3COCH_3$, and $CH_3OH$ is good but less pronounced. Only partial solubility in hexane was observed. This class of compounds, unless modified to introduce hydrophilic properties, appears to be substantially insoluble in water. The activity of compounds of this invention appears to be somewhat resistant to thermal degradation at temperatures above the melting point of the compounds (e.g. above 55° C.), and activity may survive temperatures as high as 200° C. This thermal stability can be used to advantage in commercial scale-up of the preparation of the compound from a growth medium. For example, the growth medium typically contains a large amount of water. This water can be stripped off with vacuum, but the stripping process is rather inefficient at temperatures below 40° C. At temperatures above 40° or even 50° C., reduction of water content can be carried out more effectively, and the water content can be brought down to a small percentage of its original level in a reasonably short time. This highly concentrated aqueous residue from the growth medium can then be lyophilized, extracted with ether, and chromatographed (e.g. TLC followed by HPLC) to isolate the para-anisole-containing biocide of this invention. As is known in the art, chromatography can be carried out on a commercial scale and with reasonable rates of separation using large chromatographic columns capable of handling large quantities of material. The ready solubility of the biocide in ether can be used to advantage when pure crystals of the compound are desired. In crystalline or other solid form, a biocidally effective amount of the compound can be combined with a biocidally inactive extender which may be either solid (e.g. talc or other pharmaceutically useful extenders) or liquid (e.g. ether or other organic solvents). In either a concentrated or dilute form, a compound of this invention can be stored without apparent change at below room temperature or frozen to further protect its activity. The ability to be stored in a dissolved state without apparent change at temperatures below 10° C. contrasts to some degree with the behavior of the cell extract which appeared to form precipitates when stored at 3°–5° C. or when subjected to freeze-thaw cycles. Although this invention is not bound by any theory, it is believed that the observed precipitates were proteinaceous in nature and may have carried with them some of the biocidal activity sought by this invention.

At temperatures above 40° C., some loss of activity was noted in the case of the cell extract. Again, this invention is not bound by any theory, but it is believed that compounds other than the para-anisole-containing biocide of this invention were degraded or converted or lost by exposure to such temperatures, and the para-anisole compound itself was not seriously affected.

The multi-ring structure of the para-anisole-containing biocide of this invention is presently believed to be vaguely reminiscent of other antibiotic or biocidal compounds, but, again, it must be noted that this invention is not bound by any theory. It is certainly likely to be the case that careful analogizing to other biocides and antibiotics could add to theories regarding the function of such compounds in general.

Preliminary Ames testing suggests that compounds of this invention are noncarcinogenic. Other bioassays have established activity against blue-green algae of more than one species, apparent bactericidal activity, and apparent algicidal activity against green algae which, unlike the blue-green algae, are true plants.

Uses of compounds of this invention and compositions containing them include the treatment of water supplies, swimming pools, water piping systems, filtration equipment, aquariums, and evaporation towers. Included among the water supplies which can be treated are lakes, streams, and the like. As noted previously, activity against Anabaena organisms appears to have been established, and control of Anabaena flos aquae can be of particularly great commercial importance.

EXAMPLE

The supernatent from the centifruging out of cell debris of *Scytonema hoffmanii* (University of Texas 1581) was lyophilized and extracted with diethyl ether. The ether extract was developed on a 2,000 micrometer layer of silica gel on glass using acetone and chloroform as the solvents. Approximately 2 milligrams of pure compound was obtained from the active bands from the TLC using HPLC. This 2 milligram sample was analyzed using infrared, mass spectroscopy, and high-resolution NMR. Proton NMR and mass spectroscopy confirmed the molecular weight within the range of 430 to 431 and an empirical formula of $C_{23}H_{23}O_6Cl$. The infrared showed the presence of a hydroxyl group, apparently a single OH. The NMR data showed the presence of a peculiar isopropyl group wherein the two methyl groups attached to the third carbon were not equivalent and were apparently in an asymmetric environment. The NMR further showed that a methoxy group on an aromatic ring was in a para position. The infrared spectrum further suggested the possibility of a gamma lactone group and the presence of at least three rings in the molecule including the lactone.

Additional samples of the compound were subjected to C-13 NMR which helped to provide the additional structural data set forth in this application.

The growth medium in which the cellular material which produced the aforementioned 2 milligram sample was also found to contain very small amounts of the para-anisole biocide of this invention. Apparently the Scytonema secretes small amounts of this compound or otherwise permits the compound to escape from the cellular environment.

Based upon all of the analytical data referred to in this Example, the structural formula proposed for the compound of this Example was as follows.

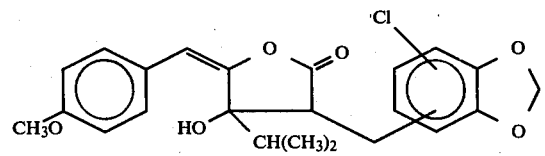

What is claimed is:

1. The substantially pure, nonsteroidal, diethylether-soluble biocidal compound $C_{23}H_{23}O_6Cl$ having a molecular weight of 430 and a melting point within the range of 48° to 55° C., and containing at least the following functional groupings:
   (a) a para-linked anisole group,
   (b) a saturated gamma-lactone,
   (c) an aliphatic hydroxyl group,
   (d) a methylene bridge,
   (e) a chlorine atom substituted on a $C_6$ aromatic nucleus, and
   (f) an isopropyl substituent in an asymmetric environment.

2. The compound of claim 1 which has been solvent extracted from a toxin produced by the species *Scytonema hoffmanii*.

3. The compound

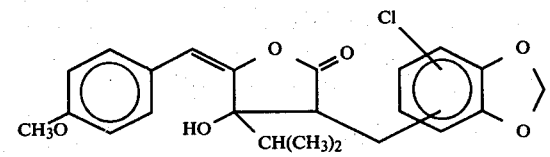

4. A composition suitable for use as a blue-green algae biocide, said composition comprising a biocidal amount of the compound of claim 1 combined with a biocidally inactive extender.

5. A method for inhibiting the growth of blue-green algae comprising the step of exposing the algae to the composition of claim 4 in a growth-inhibiting effective amount.

* * * * *